(12) United States Patent
Schneider et al.

(10) Patent No.: US 6,172,206 B1
(45) Date of Patent: Jan. 9, 2001

(54) CRYSTALLINE FORM OF MORPHINE-6-GLUCURONIDE

(75) Inventors: Herwig Schneider; Rudolph Franzmair; Andreas Koch; Franz Rovensky, all of Linz (AT)

(73) Assignee: CeNeS Ltd., Cambridge (GB)

(*) Notice: Under 35 U.S.C. 154(b), the term of this patent shall be extended for 0 days.

(21) Appl. No.: 09/433,555

(22) Filed: Nov. 4, 1999

Related U.S. Application Data

(63) Continuation of application No. 09/051,083, filed as application No. PCT/GB96/02502 on Oct. 11, 1996, now abandoned.

(30) Foreign Application Priority Data

Oct. 11, 1995 (AT) ................................. A 1683/95

(51) Int. Cl.$^7$ ........................... C07H 17/00; A61K 31/70
(52) U.S. Cl. ...................... 536/17.4; 536/18.1; 536/18.5; 514/27
(58) Field of Search ................. 536/17.4, 18.1, 536/18.5, 119; 514/27

(56) References Cited

U.S. PATENT DOCUMENTS

| | | | |
|---|---|---|---|
| 5,621,087 | * | 4/1997 | Scheinmann et al. .............. 536/17.4 |
| 5,977,326 | * | 11/1999 | Scheinmann et al. ................ 536/4.4 |
| 6,046,313 | * | 4/2000 | Scheinmann et al. ................ 536/4.4 |

FOREIGN PATENT DOCUMENTS

WO 93 05057  3/1993 (WO).

OTHER PUBLICATIONS

Oguri et al. Chem. Pharm. Bull. 1970, 18(1), 209–210.*
Yoshimura et al. Tetrahedron Letters 1968, (4), 483–6.*
Chem. Pharm. Bull., vol. 16, 1968, pp. 2114–19, XP002024005, Yoshimura et al.: "Metabolism of Drugs. LX. The Synthesis of Codeine and Morphine Glucuronides" cited in the application (see the whole document).

* cited by examiner

Primary Examiner—Kathleen K. Fonda
(74) Attorney, Agent, or Firm—Bacon & Thomas

(57) ABSTRACT

A new crystalline form of morphine-6-glucuronide, referred to as Form A, characterized by its infrared spectrum pattern and/or by its x-ray powder diffraction image, the use thereof and a process for the preparation thereof.

7 Claims, 1 Drawing Sheet

CRYSTALLINE FORM OF MORPHINE-6-GLUCURONIDE

This application is a continuation application of pending U.S. application Ser. No. 09/051,083 filed Jul. 14, 1998, which is a 371 of PCT/GB96/02502 filed Oct. 11, 1996 now abandoned.

The invention relates to a new crystalline form of morphine-6-glucuronide (M6G), known as Form A, its use and a process for preparing it.

Morphine-6-glucuronide, a metabolite of morphine, has a powerful analgesic effect.

The preparation of morphine-6-glucuronide by Könisgs-Knorr Synthesis has already been described by H. Yoshimura et al. (Chem. Pharm. Bull. 1968, 16, 2114–2119 and Tetrahedron Letters 1968, 4, 483–486), P. A. Carrupt et al. (J. Med. Chem. 1991, 34, 1272–1275) and C. Lacy et al. (Tetrahedron Letters 1995, 36, 22, 3939–3950).

F. Scheinmann et al. (EP 597915) describe the preparation thereof using the imidate method (cf. Fischer et al., J. Org. Chem. 1984, 49, 4988), which is supposed to result in reduced contamination with heavy metals.

A. Mertz et al. (WO 93/05057) describe the synthesis of morphine glucuronides from morphine and protected halogenated glucuronic acid esters with subsequent hydrolysis with alkali metal salts.

In addition, morphine-6-glucuronide has been prepared by selective enzyme-catalysed hydrolysis of morphine-3,6-diglucuronide (R. T. Brown et al., Tetrahedron Letters 1995, 36, 1117–1120).

The methods of purifying and totally removing inorganic contaminants described consist of column chromatography (C. Lacy et al.) and recrystallisation from alcohol/water mixtures (H. Yoshimura et al., P. A. Carrupt et al.).

As a result of the methods of production mentioned above, morphine-6-glucuronide is obtained in the form of crystalline compounds which form stable solvates with the solvents used in purification (methanol, ethanol, dioxan or acetonitrile). Since the recrystallisations described correspond rather to a precipitation process (the addition of alcohol reduces the polarity of the aqueous solution and leads to crystallisation), there is only a limited removal of inorganic salts as they also crystallise out.

The solvent forms thus obtained are very hygroscopic and absorb up to 20% water. However, on account of their high content of residual solvent—up to several percent by weight—the solvates are unsuitable for pharmaceutical use, particularly when the solvents in question are toxic solvents such as methanol, dioxan or acetonitrile.

There is therefore a need to produce morphine-6-glucuronide in a solvent-free crystalline form. This solvent-free form of morphine-6-glucuronide should be superior to the solvent forms in its purity, stability and physical/chemical properties. Moreover, the method of producing morphine-6-glucuronide should also be feasible on an industrial scale. In particular, the solvent used should be water.

It has now been found, unexpectedly, that morphine-6-glucuronide can be produced in a new crystalline form having improved properties by a method of preparation which conforms to the requirements described above. According to the invention, therefore, morphine-6-glucuronide is prepared in a new crystalline form which is known as Form A. It has been found that, in spite of its excellent solubility in water, morphine-6-glucuronide can be crystallised from water under certain conditions. Form A thus produced has lower heavy metal residues and organic impurities such as solvent residues and related organic substances, compared with solvent-containing forms, it is more stable and is easier to handle owing to its lower hygroscopicity and water adsorption.

Figure 1:
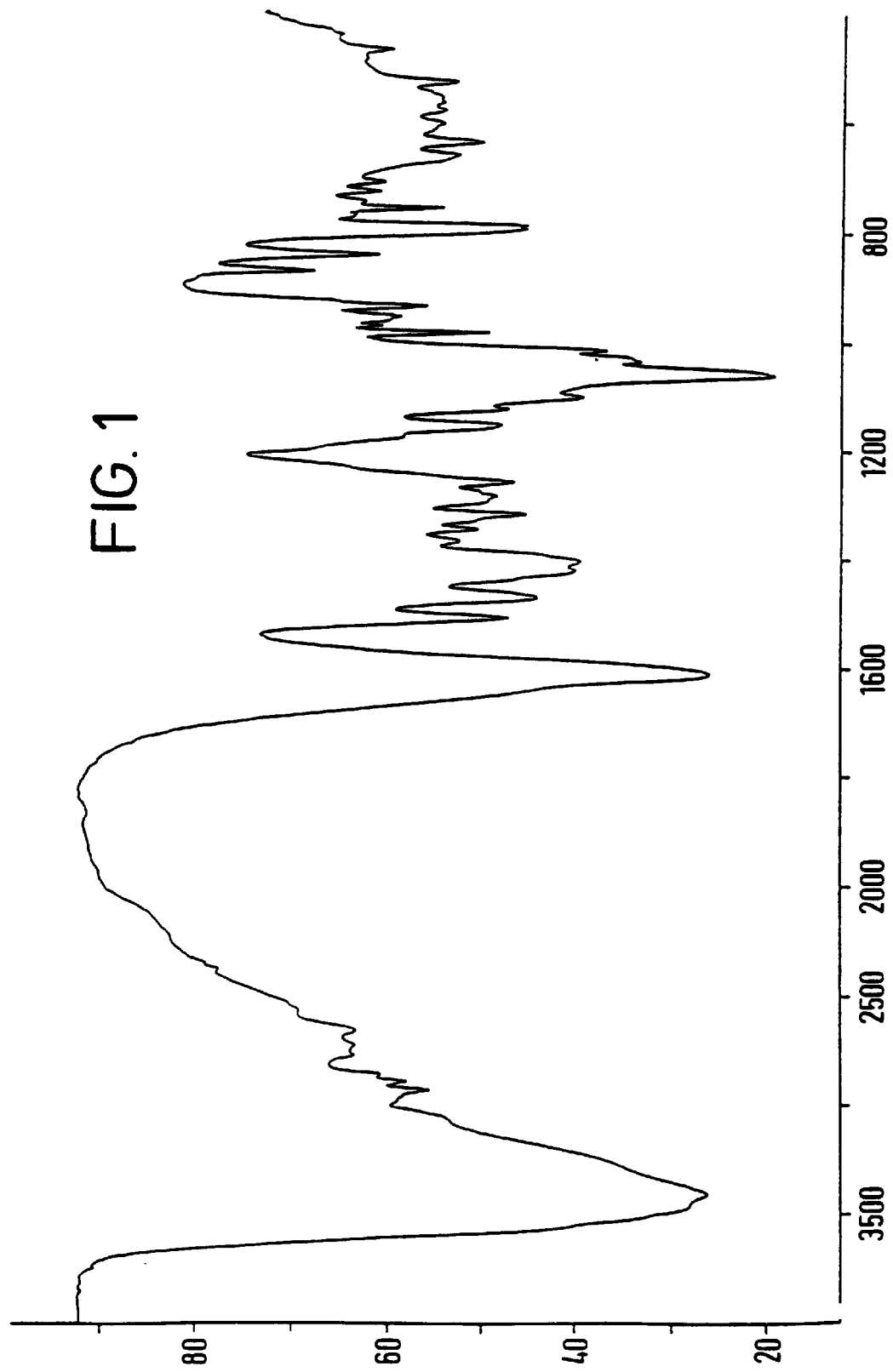
FIG. 1 is an infrared spectrum of crystalline morphine-6-glucuronide of the present invention.

The new Form A of morphine-6-glucuronide can be characterised by its infrared spectrum and by its x-ray powder diffraction image, as will be explained hereinafter.

The invention therefore relates to a new crystalline form of morphine-6-glucuronide, known as Form A, with an infrared spectrum (KBr plates) with the following main peaks:

| | |
|---|---|
| 3400 | 1060 |
| 2920 | 1020 |
| 2880 | 985 |
| 2845 | 935 |
| 1610 | 870 |
| 1505 | 840 |
| 1470 | 790 |
| 1420 | 760 |
| 1400 | 660 |
| 1260 | 640 |
| 1155 | 525 cm$^{-1}$ |
| 1105 | |

The infrared spectrum of this Form A, which is obtained according to Example 1, is shown in FIG. 1, in which the x axis shows the wave number (cm$^{-1}$) and the y axis indicates permeability.

The x-ray powder diffraction pattern of Form A of morphine-6-glucuronide can be obtained by fixing the material on an x-ray permeable carrier and photographing the image or pattern in a Guinier-de Wolff camera by illuminating for 6 hours with CuK$_{\alpha 1}$-radiation. The average value measured for the x-ray wavelength which was used for the calculations was 1.54050 Å. The x-ray powder diffraction image of Form A of morphine-6-glucuronide, expressed as "d" intervals and relative observed intensities (I$_{obs}$), is as follows (s=strong, m=medium, w=weak, v=very, d=diffuse):

| d (Å) | I$_{obs}$ | d (Å) | I$_{obs}$ |
|---|---|---|---|
| 10.518421 | m | 3.507856 | w |
| 9.555722 | m | 3.473911 | vw |
| 9.347691 | m | 3.300012 | m |
| 9.020460 | w | 3.270051 | w |
| 8.003157 | w | 3.143124 | vw |
| 6.898302 | vs | 3.113572 | m |
| 6.678446 | w | 2.966280 | m |
| 6.554282 | md | 2.835742 | s |
| 6.309124 | vw | 2.815796 | wd |
| 6.072258 | w | 2.779654 | md |
| 5.813260 | vs | 2.701992 | w |
| 5.450617 | w | 2.688437 | w |
| 5.320214 | vw | 2.652100 | wd |
| 5.195968 | w | 2.572548 | s |
| 5.064255 | md | 2.533824 | sd |
| 4.957970 | m | 2.518047 | vwd |
| 4.871266 | m | 2.500930 | vwd |
| 4.741054 | md | 2.482534 | s |
| 4.513697 | vw | 2.437035 | w |
| 4.404392 | vw | 2.249553 | vs |
| 4.307431 | w | 2.219137 | m |
| 4.267524 | vw | 2.182040 | w |
| 4.203408 | w | 2.106317 | md |

-continued

| d (Å) | $I_{obs}$ | d (Å) | $I_{obs}$ |
|---|---|---|---|
| 3.975454 | w | 2.060768 | m |
| 3.906257 | md | 1.931605 | vw |
| 3.822676 | vw | 1.908806 | vw |
| 3.782239 | vw | 1.749272 | md |
| 3.652414 | s | 1.703910 | md |
| 3.572967 | vw | | |

In contrast to the powder diffraction image of Form A shown above, the ethanol solvate of morphine-6-glucuronide has the following x-ray powder diffraction pattern photographed under the same conditions:

| d (Å) | $I_{obs}$ | d (Å) | $I_{obs}$ |
|---|---|---|---|
| 9.923882 | w | 3.275457 | st |
| 8.224315 | vw | 3.113572 | vw |
| 8.036401 | vw | 3.082198 | m |
| 7.754598 | w | 3.005415 | w |
| 7.463098 | s | 2.964076 | vw |
| 6.855597 | m | 2.957483 | vw |
| 6.724779 | vw | 2.923898 | w |
| 6.554282 | m | 2.871365 | wd |
| 6.366053 | m | 2.799069 | w |
| 6.278502 | m | 2.769095 | wd |
| 6.154070 | w | 2.696553 | m |
| 5.942185 | m | 2..649482 | m |
| 5.883685 | s | 2.642526 | vw |
| 5.273371 | vw | 2.572548 | m |
| 5.107402 | w | 2.540193 | w |
| 5.034813 | st | 2.523546 | vw |
| 4.923538 | wd | 2.506350 | vw |
| 4.656244 | w | 2.496304 | vw |
| 4.561106 | vw | 2.464420 | m |
| 4457094 | vw | 2.424666 | w |
| 4.377289 | w | 2.403870 | w |
| 4.338464 | w | 2.373720 | wd |
| 4.246699 | w | 2.321682 | vw |
| 4.154390 | w | 2.313134 | vw |
| 4.074522 | m | 2.049584 | w |
| 4.014076 | s | 2.026620 | w |
| 3.969425 | w | 2.006617 | w |
| 3.927739 | m | 2.000363 | w |
| 3.888859 | w | 1.946386 | w |
| 3.839474 | m | 1.941431 | vw |
| 3.762347 | vw | 1.914450 | vw |
| 3.723197 | vw | 1.907941 | vw |
| 3.674558 | m | 1.889124 | vw |
| 3.602342 | m | 1.879031 | vw |
| 3.572967 | vw | 1.843418 | w |
| 3.421275 | s | 1.827933 | w |
| 3.405068 | vw | 1.809265 | w |
| 3.330542 | | | |

Form A of morphine-6-glucuronide according to the invention has a lower water uptake, compared with the solvent forms, of less than 15% by weight and an improved 6-month stability of more than 97%.

Form A of morphine-6-glucuronide may be formulated in any desired type of preparation for administration. Form A of morphine-6-glucuronide according to the invention is thus used to prepare pharmaceutical compositions suitable for human or veterinary medicine. Such pharmaceutical compositions may be made up using conventional galenic excipients and/or carriers or diluents and may if necessary contain other therapeutically useful active substances.

Form A of morphine-6-glucuronide may be administered by the oral route in the form of tablets or capsules containing a single dose of the compound together with excipients and diluents such as corn starch, calcium carbonate, dicalcium phosphate, alginic acid, lactose, magnesium stearate, primogel or talc. The tablets are produced in the conventional manner by granulating the ingredients and compressing them and capsules are produced by packing into hard gelatin capsules of suitable size. Form A of morphine-6-glucuronide may also be administered in the form of suppositories which contain excipients such as beeswax derivatives, polyethyleneglycol or polyethyleneglycol derivatives, linoleic or linolenic acid esters, together with a single dose of the compound, and are administered by the rectal route.

Form A of morphine-6-glucuronide may also be administered parenterally, e.g. by intramuscular, intravenous or subcutaneous injection. For parenteral administration it is best used in the form of a sterile aqueous solution which may contain other dissolved substances such as tonic agents, agents for adjusting the pH, preservatives and stabilisers. The compound may be added to distilled water and the pH may be adjusted to 3 to 6 using, for example, citric acid, lactic acid or hydrochloric acid. Adequately dissolved substances such as dextrose or saline solution may be added to render the solution isotonic. In addition, preservatives such as p-hydroxybenzoates and stabilisers such as EDTA may be added to ensure that the solution is sufficiently stable and durable. The solution thus obtained can then be sterilised and transferred into sterile glass ampoules of a suitable size so as to contain the desired volume of solution. Form A of morphine-6-glucuronide may also be administered by infusion of a parenteral formulation as described above.

Form A of morphine-6-glucuronide according to the invention may also be administered in the form of an oily preparation, a buffered or unbuffered emulsion, a gel or a cream, or by means of a transdermal plaster.

For oral administration in humans, it is assumed that the daily dosage is in the range from 0.001 to 100 mg per day for a typical adult patient weighing 70 kg. Therefore, tablets or capsules may generally contain 0.0003 to 30 mg of active compound, for example 0.01 to 5 mg, for oral administration up to three times a day. For parenteral administration, the dosage may range from 0.001 to 100 mg per 70 kg per day, for example about 0.5 mg.

The invention also relates to a process for preparing Form A of morphine-6-glucuronide.

Form A of morphine-6-glucuronide may be prepared by crystallisation under controlled conditions. The starring material may be either solvate-free morphine-6-glucuronide or any desired morphine-6-glucuronide solvate.

For recrystallisation, morphine-6-glucuronide is dissolved in 2 to 10 times the quantity of water, with heating and stirring. If the starting material is morphine-6-glucuronide solvate, it may be refluxed in order to distil off any residual solvent. The solution thus prepared can be filtered in order to ensure total removal of insoluble ingredients, e.g. using a glass filter or a membrane filter. The particle size of the crystals may be controlled by suitably selecting the rate of cooling and the speed of stirring.

It has proved advisable to add seed crystals of the desired shape to the crystallisation solution and to stop stirring when crystallisation begins. Crystallisation is carried out by cooling a solution at, for example, 40–80° C. to about 0–30° C. over a fairly long period, for example 15–360 minutes. Form A of morphine-6-glucuronide thus obtained can be isolated by centrifuging or filtering and washed with water.

EXAMPLES

Example 1
Preparation of Form A from morphine-6-glucuronide solvate 1.12 kg of morphine-6-glucuronide are dissolved in 4000 ml of water with heating and heated to boiling for 5–10 minutes with stirring. The solution is filtered and the filter is washed with 500 ml of water. The solution is cooled to 4° C. over a period of 50 minutes and maintained at 4° C. for 8 hours. The crystals obtained are filtered off, washed three times with a total of 700 ml of ice cold water and dried for 4–10 hours at 75° C. under reduced pressure, to obtain Form A of morphine-6-glucuronide (0.92 kg of crystalline powder).

Mp: 243–246° C. (decomposition).

Example 2
Preparation of a solvate form of morphine-6-glucuronide 1.17 kg of morphine-6-glucuronide is dissolved in 5800 ml of water at boiling temperature, boiled for S minutes, filtered and combined with 7600 ml of hot (70° C.) ethanol, whereupon crystallisation (precipitation) sets in very quickly. Within 30 minutes the mixture is cooled to ambient temperature and maintained for 2 hours at ambient temperature and then for 20 hours at 4° C. The solid obtained is filtered off, washed three times with a total of 2200 ml of ethanol/water mixture (4:3) and 1000 ml of ethanol and dried for 3 hours under reduced pressure.

Yield: 1.05 kg of crystalline powder.

Mp: 250–252° C. (decomposition).

Example 3
Stability

Different samples of the new crystalline form and the known solvate form (ethanol) of the same quality are stored at a temperature of 25° C. and a relative humidity of 60% in polyethylene bottles. The measurements of the contents were carried out using HPLC.

|  | Start | 1 month | 3 months | 6 months |
|---|---|---|---|---|
| EtOH-Solvate content | 98.9% | 97.0% | 95.4% | 89.7% |
| Form A content | 99.4% | 99.1% | 99.2% | 99.2% |

Example 4
Hygroscopicity

The samples were stored at constant relative humidity until a constant weight was achieved. The data are provided in percent by weight of water and corrected for the water content of the form used.

| Relative humidity | 10% | 20% | 30% | 40% | 50% | 60% | 70% | 80% | 90% |
|---|---|---|---|---|---|---|---|---|---|
| EtOH-solvate | 11.4% | 12.1% | 16.0% | 17.0% | 17.2% | 17.5% | 17.7% | 17.8% | 17.7% |
| Form A | 7% | 7.3% | 7.6% | 8.0% | 7.9% | 8.1% | 9.1% | 11.8% | 12.5% |

What is claimed is:

1. Crystalline morphine-6-glucuronide having an infrared spectrum (KBr plates) with the following main peaks:

| | |
|---|---|
| 3400 | 1060 |
| 2920 | 1020 |
| 2880 | 985 |
| 2845 | 935 |
| 1610 | 870 |
| 1505 | 840 |
| 1470 | 790 |
| 1420 | 760 |
| 1400 | 660 |
| 1260 | 640 |
| 1155 | 525 $cm^{-1}$ |
| 1105 | | and an x-ray powder diffraction pattern, expressed by "d" intervals and relative intensities I as follows:

| d (Å) | $I_{obs}$ | d (Å) | $I_{obs}$ |
|---|---|---|---|
| 10.518421 | m | 3.507856 | w |
| 9.555722 | m | 3.473911 | vw |
| 9.347691 | m | 3.300012 | m |
| 9.020460 | w | 3.270051 | w |
| 8.003157 | w | 3.143124 | vw |
| 6.898302 | vs | 3.113572 | m |
| 6.678446 | w | 2.966280 | m |
| 6.554282 | md | 2.835742 | s |
| 6.309124 | vw | 2.815796 | wd |
| 6.072258 | w | 2.779654 | md |
| 5.813260 | vs | 2.701992 | w |
| 5.450617 | w | 2.688437 | w |
| 5.320214 | vw | 2.652100 | wd |
| 5.195968 | w | 2.572548 | s |
| 5.064255 | md | 2.533824 | sd |
| 4.957970 | m | 2.518047 | vwd |
| 4.871266 | m | 2.500930 | vwd |
| 4.741054 | md | 2.482534 | s |
| 4.513697 | vw | 2.437035 | w |
| 4.404392 | vw | 2.249553 | vs |
| 4.307431 | w | 2.219137 | m |
| 4.267524 | vw | 2.182040 | w |
| 4.203408 | w | 2.106317 | md |
| 3.975454 | w | 2.060768 | m |
| 3.906257 | md | 1.931605 | vw |
| 3.822676 | vw | 1.908806 | vw |
| 3.782239 | vw | 1.749272 | md |
| 3.652414 | s | 1.703910 | md |
| 3.572967 | vw | | | and which has a melting point of 243–246° C. (decomposition).

2. A process for preparing the morphine-6-glucuronide according to claim 1, wherein morphine-6-glucuronide is crystallized from water by dissolving said glucuronide by heating and crystallizing out said glucuronide.

3. A process according to claim 2 wherein the morphine-6-glucuronide is dissolved in 2–10 times the quantity of water at a temperature of 40–100° C. and subsequently crystallized out by cooling to 0–30° C. over a period of 15–360 minutes.

4. The morphine-6-glucuronide prepared by the process of claim 2.

5. The morphine-6-glucuronide prepared by the process of claim 3.

6. Morphine-6-glucuronide according to claim 1, which takes up less than 15% water at relative humidities of 10–90%.

7. Morphine-6-glucuronide according to claim 1, wherein the 6-month stability of said morphine-6-glucuronide is at least 97% at a temperature of 25° C. and a relative humidity of 60%.

* * * * *